United States Patent [19]

Haas et al.

[11] Patent Number: 5,679,860
[45] Date of Patent: Oct. 21, 1997

[54] PROCESS FOR THE PRODUCTION OF 3-AMINOETHYL-3,5,5-TRIMETHYLCYCLOHEXYL AMINE

[75] Inventors: Thomas Haas, Frankfurt; Roland Burmeister, Geiselbach; Dietrich Arntz, Oberursel; Karl-Ludwig Weber, Dieburg; Monika Berweiler, Maintal, all of Germany

[73] Assignee: Degussa Aktiengesellschaft, Germany

[21] Appl. No.: 739,044

[22] Filed: Oct. 28, 1996

[30] Foreign Application Priority Data

Oct. 30, 1995 [DE] Germany .................. 195 40 191.3

[51] Int. Cl.$^6$ .................. C07C 209/32; C07C 209/48
[52] U.S. Cl. .................. 564/448; 564/461
[58] Field of Search .................. 564/448, 461

[56] References Cited

U.S. PATENT DOCUMENTS

| | | | |
|---|---|---|---|
| 3,352,913 | 11/1967 | Schmitt et al. | 260/563 |
| 3,558,365 | 1/1971 | Duddy | 136/120 |
| 3,781,227 | 12/1973 | Sokolsky et al. | 252/466 |
| 4,826,799 | 5/1989 | Cheng et al. | 502/301 |
| 5,091,554 | 2/1992 | Huthmacher et al. | 558/341 |
| 5,504,254 | 4/1996 | Haas et al. | 564/446 |
| 5,536,694 | 7/1996 | Schuetz et al. | 502/301 |

FOREIGN PATENT DOCUMENTS

| | | |
|---|---|---|
| 0 091 027 | 10/1983 | European Pat. Off. . |
| 0 042 119 | 3/1984 | European Pat. Off. . |
| 0 394 967 | 10/1990 | European Pat. Off. . |
| 0 449 089 | 10/1991 | European Pat. Off. . |
| 2 100 373 | 9/1972 | Germany . |
| 2 139 774 | 4/1973 | Germany . |
| 2 101 856 | 10/1973 | Germany . |
| 2 053 799 | 6/1974 | Germany . |
| 28 29 901 | 1/1990 | Germany . |
| 44 26 472 | 2/1995 | Germany . |

OTHER PUBLICATIONS

JP Patent Appln. Disclosure 7-188126—Jul. 25, 1995.
JP Patent Appln. Disclosure 6-321870—Nov. 22, 1994.
JP Patent Appln. Disclosure 99 987/75—Aug. 8, 1975.

*Primary Examiner*—Peter O'Sullivan
*Attorney, Agent, or Firm*—Beveridge, DeGrandi, Weilacher & Young, L.L.P.

[57] ABSTRACT

A process for producing 3-aminomethyl-3,5,5-trimethylcyclohexyl amine (isophorone diamine) from isophorone nitrile. Isophorone nitrile is iminated in a first stage and then the reaction mixture is subjected to aminating hydrogenation in a second stage in the presence of a fixed bed hydrogenation catalyst based on Raney cobalt. The fixed bed hydrogenation catalyst is produced in a special manner by mixing a powdery Co—containing Raney alloy with powdery cobalt, sintering the powdery mixture to shaped moldings and then activating by leaching with alkali hydroxide solution. The yield and/or space-time yield in isophorone diamine production can be increased.

11 Claims, No Drawings

5,679,860

PROCESS FOR THE PRODUCTION OF 3-AMINOETHYL-3,5,5-TRIMETHYLCYCLOHEXYL AMINE

INTRODUCTION AND BACKGROUND

The present invention relates to an improved process for producing 3-aminomethyl-3,5,5-trimethylcyclohexyl amine, also referred to below as isophorone diamine or IPDA, from 3-cyano-3,5,5-trimethylcyclohexanone, also referred to below as isophorone nitrile or IPN.

In a further aspect, the present invention relates to a process comprising a first stage for the at least partial conversion of isophorone nitrile into isophorone nitrile imine and a second stage for the aminating hydrogenation of the reaction mixture of the first stage with hydrogen and ammonia in the presence of a lower alcohol and a fixed bed hydrogenating catalyst based on Raney cobalt. The process according to the invention permits the continuous production of isophorone diamine in high purity with higher yield and/or higher space-time yield than prior known two-stage processes.

Isophorone diamine has a number of significant utilities, including as a starting product for the production of isophorone diisocyanate systems, which is an isocyanate component for polyurethane systems as an amine component for polyamides and as a hardener for epoxy resins. Isophorone diamine is produced conventionally from isophorone nitrile, in which the carbonyl group is converted into an amino group and the nitrile group into an aminomethyl group in the presence of ammonia, hydrogen and conventional hydrogenation catalyst. The starting product isophorone nitrile can be obtained in conventional manner by the addition of hydrogen cyanide to isophorone; see German published application 39 42 371 corresponding to U.S. Pat. No. 5,091,554.

According to the process for producing isophorone diamine from isophorone nitrile described in U.S. Pat. No. 3,352,913, the hydrogenation takes place in the presence of ammonia and in the presence of known catalyst; i.e. cobalt-, nickel-, iron-, or noble metal-containing catalysts at 50° to 150° C. and a pressure of at least 50 bar. For example, the hydrogenation takes place in the presence of methanol as solvent with the use of suspended and fixed bed catalysts. In addition to the desired isophorone diamine, large amounts of by-products are also obtained, e.g. in particular 3-aminomethyl-3,5,5-trimethylcyclohexylanol (isophorone amino alcohol, IPAA). The low yield and the considerable proportion of by-products formed in the known methods proved to be disadvantages of this system.

In an attempt to obtain a higher yield of IPDA and to minimize the unavoidable incidence of IPAA, the German published application 30 11 656 reveals a two-stage process, in which in the first stage IPN is converted catalyst-free with surplus ammonia into 3-cyano-3-5,5-trimethyl-iminocyclohexane and the latter is then hydrogenated to IPDA in the second stage. A disadvantage of this process is that in addition to the actual hydrogenation reactor a special imine formation reactor is required.

According to EP-B 0 042 119 it is regarded as a further improvement of the known process to subject the isophorone nitrile, prior to the reaction of the latter with ammonia and hydrogen in the presence of hydrogenation catalysts at temperatures of 10° to 120° C. and pressures of 1 to 300 bar, to a preliminary reaction with ammonia in the presence of inorganic and organic ion exchangers in the ammonium form as imine formation catalysts. Whereas the ratio by volume of isophorone nitrile to ammonia is to vary between 1 and 0.5 to 20 in the imine formation stage, this ratio is increased to between 1 and 10 to 20 in the hydrogenation stage. Although the process, which can be carried out in trickle bed reactors, certainly leads to a high yield of IPDA and to a high purity, the profitability of the process is impaired by the high surplus of ammonia, which requires a very high pressure and hence makes sophisticated hydrogenation equipment necessary.

According to German application 44 26 472 of DuPont it is also possible for isophorone nitrile to be converted with the use of a supported heteropoly acid catalyst with ammonia into the isophorone nitrile amine and for the latter to be converted into isophorone diamine with the use of conventional fixed bed hydrogenation catalysts, including also Raney® cobalt. The high hydrogenating pressures required in practice—for example 238 bar—are disadvantageous, which calls for highly sophisticated equipment.

In EP-B 0 042 19 a comparative example is also disclosed in which isophorone nitrile and liquid ammonia are pumped from above into a fixed bed hydrogenation reactor charged with commercial cobalt catalysts. The reaction system is held at 270 bar with $H_2$. There is obtained with this single-stage form of execution, despite roughly quantitative conversion of the isophorone nitrile, after working up by distillation only 48% of isophorone diamine together with many by-products. According to German application 43 43 890 corresponding to U.S. Pat. No. 5,504,254 the pressure was able to be reduced to 3 to 10 MPa by the use of a $C_1$—to $C_3$— alcohol as solvent. With a trickle bed method of operation a yield of just under 90% was achieved with an LHSV value of $1h^{-1}$ (liquid hourly space velocity) and without recycling of recrackable high-boiling by-products.

A further two-stage process for producing isophorone diamine is known from EP-A 0 449 089: in two reaction chambers physically separated from one another a solution of isophorone nitrile is first of all reacted in tetra-hydrofuran with surplus ammonia on acid metal catalysts and the reaction mixture is hydrogenated in a second reaction chamber with hydrogen in the presence of surplus ammonia on cobalt-, nickel-, ruthenium- and/or other noble metal-containing catalysts and optionally basic components at very high pressure. The high pressure makes very sophisticated hydrogenation equipment necessary.

EP-A 0 394 967 also covers the production of isophorone diamine from isophorone nitrile, wherein IPN is first of all converted into the aminonitrile under conditions of reduced amination in the presence of a first hydrogenation catalysts at moderate temperatures and the nitrile group is then converted into an aminomethyl group at higher temperature in the presence of a second hydrogenation catalyst having a hydrogenating effect towards nitrile groups. Although this process can be carried out at low pressures, it is regarded as a major disadvantage that a strict temperature regime has to be observed during the two reaction stages, as a result of which the space-time yield and hence the profitability of the process decline. Unless special promoters are additionally used, the IPDA product excessively high content in 3-cyano-3,5,5-trimethylaminocyclohexane, which is impossible to separate by distillation.

In the process according to JP-A 06-321870 an equilibrium mixture of isophorone nitrile imine obtained from isophorone nitrile in the absence of an imination catalyst, but in the presence of methanol and ammonia, is subjected to aminating hydrogenation in the presence of a fixed bed catalyst containing a catalyst metal from the series Co, Ni, Ru and Pd preferably Co on diatomite. The yield in IPDA is only 88%, and in addition the space-time yield is low. According to JP-A 07-188126 use is made in the aforementioned process for the aminating hydrogenation of a fixed bed catalyst based on Raney cobalt, wherein the catalyst is obtained by the elimination by melting of aluminum out of a binary or ternary Raney alloy. In this case also the yield of IPDA given in the examples comes to only some 88%.

An object of the present invention is to obtain a higher yield of IPDA and/or higher space-time yield in a two-stage process for producing IPDA and IPN. It is a further object to obtain IPDA in high product purity.

A still further object of the present invention is to carry out the hydrogenation stage at a pressure of not more than 10 MPa, preferably below 8 MPa, in order to keep the cost of equipment as low as possible.

SUMMARY OF THE INVENTION

The above and other objects are achieved by a process for producing 3-aminomethyl-3,5,5-trimethylcyclohexyl amine (isophorone diamine, IPDA) from 3-cyano-3,5,5-trimethylcyclohexanone (isophorone nitrile, IPN), comprising a first stage, in which isophorone nitrile is in the presence or absence of an imination catalyst converted with ammonia at least partially into 3-cyano-3,5,5-trimethylcyclohexanone imine, and a second stage, in which the reaction mixture of the first stage, not yet present on the whole, is, after the addition of an alcohol with 1 to 3 carbon atoms, subjected to aminating hydrogenation with hydrogen with the use of a fixed bed, special hydrogenation catalyst based on Raney cobalt at a temperature in the range from 50° to 150° C. and a pressure in the range from 3 to 10 MPa.

It is a feature of the present invention that the hydrogenation catalyst to be used is produced by a process comprising:

(i) intimately mixing at least one powdery cobalt alloy and powdery cobalt as binder, wherein the cobalt alloy contains cobalt and optionally promoters as well as a leachable alloy component from the series aluminum, zinc and silicon and the powdery mixture contains cobalt and leachable alloy components in the ratio by weight of between 30 to 70 and 75 to 25, (ii) sintering the powdery mixture to a mechanically stable molded product with a density of 1.3 to 5.5 g/cm$^3$, a pore volume up to 0.5 c$^3$/g (water adsorption) and a BET surface area (DIN 66 132) of less than 1 m$^2$/g and (iii) activating the sintered molded product by at least partially leaching out of the leachable alloy component by means of an alkali hydroxide solution.

DETAILED DESCRIPTION OF INVENTION

The fixed bed catalyst to be used according to the invention for the aminating hydrogenation of the reaction mixture obtained from the first stage and containing isophorone nitrile imine and isophorone nitrile is obtainable by the process described in German 43 35 360 (U.S. Pat. No. 5,536,694) and German 43 45 265 (U.S. Pat. No. 5,536,694). As regards the selection and physical characteristics of the raw materials to be used in the production—catalyst metal, alloy and, where required, promoters and auxiliary substances such as molding aids, lubricants, plasticizers and/or pore formers—and physical characteristics of the catalyst precursor as well as details of the process stages, namely mixing of the components, sintering of the powder mixture to moldings of the catalyst precursor and activation of the catalyst by at least partial leaching of the leachable alloy component out of the catalyst precursor, reference is made to the above-mentioned documents which are relied on and incorporated herein by reference for all relevant details.

There is given as the area of use for the catalysts described in the aforementioned documents U.S. Pat. No. 5,536,694 and U.S. Pat. No. 5,536,694 the hydrogenation of nitro groups, C—C double bonds, sugars and aromatic rings. Indications or a suggestion that imines and nitrile groups should also be subjected to aminating hydrogenation with these catalysts cannot be derived from the above-mentioned documents. It was surprising that the use of these special fixed bed catalysts based on Raney cobalt in the two-stage process according to the invention for producing IPDA from IPN leads to a higher yield with in most cases even simultaneously higher space-time yield. It was also found that corresponding catalysts based on Raney nickel are considerably less effective in the two-stage production of IPDA from IPN than those based on cobalt. Compared also with Raney cobalt fixed bed catalysts previously used, the catalysts used according to the invention showed a significantly higher catalyst effectiveness in the second stage.

In the first stage of the process according to the invention at least one part, preferably the greatest part, of the isophorone nitrile introduced is converted into isophorone nitrile imine. The reaction mixture leaving the imination stage should as far a8 possible contain isophorone nitrile imine and isophorone nitrile in a molar ratio of more than 1. The imination of the isophorone nitrile is conducted with expediency up to a conversion rate of over 80%, preferably 90%.

If the imination is carried out in the absence of an imination catalyst, several hours are required at a reaction temperature in the range between 10° and about 60° C. to achieve the desired imination rate; although it is certainly also possible for the imination to be carried out in the example at 100° C. However, there is then the risk of an increased formation of by-products, as a result of which the product purity of the isophorone diamine obtained from the reaction mixture of the second stage after recovery by distillation is adversely affected. It is advisable to use an imination catalyst in order to accelerate the establishment of equilibrium in the first stage. The imination catalyst known from the prior art can be used for this. Suitable imination catalysts, which is a well known term in the art, are acid inorganic and organic ion exchangers (see EP-B 0 042 119), acid metal oxides, such as in particular aluminum oxide and titanium oxide (anatase) (see EP-A 0 449 089), supported heteropoly acids (see German 44 26 472) and acid zeolites. If an imination catalyst is used, the reaction temperature can lie in the range between 10° and 150° C., preferably between 60° and 130° C. and in particular between 80° and 120° C.

Although the imination of isophorone nitrile with liquid ammonia in the absence of a further solvent is possible, it has proved to be advantageous to use additionally an organic solvent from the series of an alcohol with 1 to 3 carbon atoms, preferably of a monovalent primary alcohol and in particular methanol. Preferably there is fed to the imination reactor a mixture containing isophorone nitrile, liquid ammonia and methanol. The mixture contains 10 to 40 wt. %, preferably to 10 to 30 wt. %, of isophorone nitrile and 10 to 40 wt. %, preferably 20 to 40 wt. %, of ammonia. It is advantageous to mix isophorone nitrile, ammonia and the alcohol together in a ratio such that an essentially homogeneous solution is obtained. In principle the aforementioned limiting values for ammonia and isophorone nitrile can also be fallen short of or exceeded, if an essentially homogeneous solution is thereby obtained.

In the case of imination in the presence of an imination catalyst, the catalyst can be used in the form of a suspended catalyst or a fixed bed catalyst. The use of a fixed bed catalyst is advantageous, since elaborate steps for the separation of the reaction mixture from the catalyst then become superfluous. In the case of imination of isophorone nitrile in the presence of a fixed bed catalyst the latter is employed in the form of conventional catalyst moldings, such as extrusion moldings, pellets and tablets, as a bed in a fixed bed reactor. The imination catalyst can be arranged in its own reactor. It is also possible, however, to arrange the imination catalyst in a reactor which contains both a bed of the imination catalyst and a bed of the catalyst used for the aminating hydrogenation. Depending on whether the reactor is operated as a trickle bed reactor or as a bubble reactor, the bed of the imination catalyst is located above (trickle bed) or below (bubble reactor) the bed of the hydrogenation catalyst. It has proved to be advantageous to use a single reactor which contains a bed of the hydrogenation catalyst and a bed of the imination catalyst; preferably such a reactor is operated in the form of a trickle bed reactor. The mixture of isophorone nitrile, liquid ammonia and alcohol, in particular methanol, is then supplied at the reactor head. In these cases hydrogen advantageously flows into the reactor simultaneously from above for the aminating hydrogenation.

In addition to the aforementioned components of the mixture to be fed to the imination stage, the latter can contain additionally fractions with a higher or lower boiling point than isophorone diamine from the recovery by distillation of the reaction mixture drawn off from the trickle bed reactor. Such fractions can also contain, in addition to residues of isophorone diamine, by-products from which isophorone diamine again forms under the reaction conditions. The yield in isophorone diamine can be increased substantially by returning fractions of this kind into the mixture to be used. It is particularly advantageous to feed to the trickle bed reactor the fraction with a boiling point above isophorone diamine, which in addition to residues of isophorone diamine contains 3,3,5-trimethyl-6-imino-7-azabicyclo-[3,2-1]-octane as main product, together with the mixture of isophorone nitrile, ammonia and solvent. The recycling of the fraction containing the above-mentioned by-product—a bicyclic compound of amidine structure—makes it possible to considerably increase the yield of isophorone diamine and hence to enhance the profitability of the process. The fraction containing the cyclic amidine can, if this is desired, also be added directly to the reaction mixture to be fed to the second stage.

The catalyst used in the second stage of the process according to the invention is a fixed bed catalyst. Conventional fixed bed reactors are used to carry out this process stage. As already mentioned in connection with the imination stage, the reactor can be operated both as a trickle bed reactor and as a bubble column, although, as follows also from German 43 43 390, the trickle bed method of operation is preferred.

The layouts and arrangement of suitable reactors are known to those skilled in this art. Thus, the fixed bed catalyst is arranged in a vessel in the form of one or more beds; the reactor also possesses devices for controlling the temperature of the catalyst beds, in order to ensure that the desired temperature is maintained in the particular catalyst bed. Instead of a single trickle bed reactor, several trickle bed reactors can also be connected one behind the other, wherein the reaction mixture leaving the first reactor is charged again at the head of the second reactor. The trickle bed reactor or reactors also possess suitable devices for charging the reaction mixture and the hydrogen, also devices for distributing the liquid over the surface of the first catalyst bed and finally suitable removal devices for the reaction mixture leaving the reactor.

The aminating hydrogenation, i.e. the second reaction stage, is carried out at a temperature in the range of 50° to 150°, preferably 80° to 150° C. and most preferably 90° to 130° C. The aminating hydrogenation takes place at a pressure in the range of 3 to 10 MPa, preferably at 5 to 8 MPa and in particular below 8 MPa. Due to the above-mentioned moderate operating pressures, which are possible with the use of the claimed mixtures of isophorone nitrile, ammonia and solvent and the trickle bed method of operation under the claimed temperature conditions, the investment needed is reduced and hence the profitability increased compared with processes which require a high operating pressure. By the specified pressure is meant the overall pressure, which is the sum of the partial pressures of ammonia, hydrogen $C_1$—$C_3$—alcohol and the other components of the reaction mixture.

The volume of fixed bed catalyst required for the second stage is determined by the LHSV value (liquid hourly space velocity), which is dependent on the operating pressure, the temperature and the catalyst activity and must be adhered to in order to achieve as quantitative as possible a conversion of the mixture containing isophorone nitrile imine and isophorone nitrile imine and isophorone nitrile. The LHSV comes conventionally to at least $0.5\ h^{-1}$ and preferably lies in the range above $0.5\ h^{-1}$ to $3\ h^{-1}$. It is an advantage of the process according to the invention that a virtually quantitative conversion is achieved, and IPDA can be obtained in high yield and high purity, with an LHSV value of about 2 $h^{-1}$, a reaction temperature in the range between 90° and 130° C. and a pressure between 5 and less than 8 MPa. The high LHSV value leads in addition to a high space-time yield.

In the embodiment particularly preferred according to the invention, in which a trickle bed reactor contains a lower bed of hydrogenation catalyst and an upper bed of imination catalyst, the respective bed height is adjusted to the corresponding catalyst activity. The skilled person in the art can determine this activity and hence the bed height by means of simply performed preliminary tests. It follows from the examples that if titanium dioxide is used as imination catalyst, a bed height which comes to about a quarter of that of the hydrogenation catalyst is sufficient.

The hydrogen required for the hydrogenation can be fed to the reactor either in excess or in an amount such that no hydrogen has to be discharged from the reactor and recycled. Preferably hydrogen is not fed in excess, in order to avoid the technical complexities involved in the separation of this excess, the condensation of the ammonia and solvent contained in the latter, and the compression of the purified hydrogen and recycling.

The process according to the invention is distinguished by its simplicity, low investment volume, high yield, high space-time yield and high IPDA product purity.

The following examples serve to illustrate the present invention.

EXAMPLE 1

A reaction tube operated as a trickle bed reactor was filled in the lower region with 160 ml of hydrogenation catalyst and in the region lying above the latter with 40 ml of imination catalyst. Titanium dioxide (titanium dioxide P 25 of Degussa AG) in the form of 1 mm extrudates was used as imination catalyst. Activated Raney cobalt catalyst, produced according to German patent application 43 45 265.5, in the form of tablets 5 mm in height and 3 mm in diameter, was used as hydrogenation catalyst. The batch solution, which contained IPN and methanol, as well as liquid ammonia were pumped into the reaction tube from above. The hydrogen was also introduced into the reaction tube from above. The reaction temperature was held at 100° by oil heater. The pressure was set at 6 MPa. The liquid was collected in a separation vessel. The gas current at the reactor inlet was adjusted so that the whole of the hydrogen was consumed.

The batch solution contained 24 wt. % of IPN and 76 wt. % of methanol. 260 ml/h of this batch solution and 140 ml/h of ammonia were mixed directly prior to charging to the reactor and the mixture was pumped into the reactor. The LHSV value therefore came to $2h^{-1}$.

According to the analysis of the product mixture a yield of 92.2% of isophorone diamine (=IPDA), referred to IPN used, was obtained. In addition 3% of 2-aza-4,6,6-trimethyl-bicyclo-3,2,1-octane (=bicyclic compound) and 3.3% of 3,5,5-trimethyl-6-imino-7-aza-bicyclo-3,2,1-octane (=amidine) were contained in the product mixture. A product purity of 99.8% was obtained after the distillation of the liquid product mixture. Methyl-IPDA was detectable in a quantity of only 200 ppm.

It follows from a comparison with the following comparative examples 1 and 2 that the use of the hydrogenation catalyst according to the invention leads by virtue of this higher hydrogenation activity to a surprisingly high increase in the yield and space-time yield.

COMPARATIVE EXAMPLE 1

A reaction tube operated as a trickle bed was filled with 160 ml of hydrogenation catalyst in the lower region and with 40 ml of imination catalyst in the region lying above the latter. Whereas the imination catalyst corresponded to that of Example 1 ($TiO_2$ P 25 of Degussa AG), there was used as hydrogenation catalyst a commercial supported cobalt catalyst based on 50% cobalt on a silicate support (injection moldings of 4–5 mm diameter and height). The operating conditions pressure, temperature, LHSV value, flow rate and concentration of the methanolic IPN batch solution and flow rate of the liquid ammonia—corresponded to those of Example 1.

According to the analysis of the product mixture a yield of 82% of IPDA was obtained.

COMPARATIVE EXAMPLE 2

Comparative example 1 was repeated, the only difference being that the liquid flow rates were changed: 130 ml/h of methanolic IPN batch solution (24 wt. % IPN) and 70 ml/h of liquid ammonia were mixed directly prior to charging to the reactor and the mixture was pumped into the reactor. The LHSV value therefore came to $1 h^{-1}$.

According to the analysis of the product mixture a yield of 90.7% of IPDA was obtained, referred to IPN used. In addition 4% of bicyclic compound and 3.2% of amidine were contained in the product mixture. Distillation of the product mixture produced a product purity of 99.8 GC-FL. %.

The increase in the yield which still lay below that of Example 1 according to the invention, was unfortunately accompanied by a halving of the space-time yield.

COMPARATIVE EXAMPLE 3

The conversion was carried out in a similar way to Example 1, but using inert steel balls 2 mm in diameter instead of the $TiO_2$ imination catalyst. All the other test conditions conformed to Example 1.

According to the analysis of the product mixture a yield of 73.7% of IPDA was obtained.

This comparative example shows that in the absence of an effective imination catalyst, but using an activated Raney cobalt catalyst according to the invention as hydrogenation catalyst, only a moderate IPDA yield is obtained.

EXAMPLE 2

A solution containing 15 wt. % of IPN, 30 wt. % of ammonia and 55 wt. % of methanol was produced and stirred in a pressure vessel under the pressure obtained for 24 h at 25° C.; in this case isophorone nitrile (IPN) was converted largely into isophorone imino nitrile (IPIN). This solution was then pumped at 400 ml/h, corresponding to an LHSV value of $2 h^{-1}$, through the reactor, which was filled with 160 ml of hydrogenation catalyst according to the invention (as in Example 1) and 40 ml of inert steel balls. According to the analysis of the product mixture a yield of 92.1% of IPDA was obtained. After distillation of the product mixture a product purity of 99.78% IPDA was obtained.

EXAMPLE 3

In a reaction tube filled according to Example 1 the reaction—imination with subsequent hydrogenation—was carried out as per Example 1, the only difference being that an LHSV value of $1 h^{-1}$ was set. According to the analysis of the product mixture a yield of 94.2% of IPDA was obtained, referred to IPN used. In addition bicyclic compound and 1% of amidine were contained in the product mixture.

The example shows that the yield in IPDA was able to be increased still further by a lowering of the LHSV value (compared with Example 1).

Further variations and modifications will be apparent to those skilled in the art and are intended to be encompassed by the claims appended hereto.

German priority application 195 40 191.3 is relied on and incorporated herein by reference.

We claim:

1. A process for producing 3-aminomethyl-3,5,5-trimethylcyclohexyl amine from 3-cyano-3,5,5-trimethylcyclohexanone comprising in a first stage, converting said cyclohexanone in an imination reaction with ammonia at least partially into 3-cyano-3,5,5-trimethylcyclohexane imine, to form a first reaction mixture and in a second stage, after the addition of an alcohol with 1 to 3 carbon atoms, subjecting said first reaction mixture to aminating hydrogenation with hydrogen in the presence of a fixed bed hydrogenation catalyst at at a temperature in the range from 50° to 150° C. and a pressure in the range from 3 to 10 MPa,
wherein said hydrogenation catalyst is produced by a process comprising:
(i) intimately mixing at least one powdery cobalt alloy and powdery cobalt as binder to obtain a powdery mixture, wherein the cobalt alloy contains cobalt and optionally promoters as well as a leachable alloy component selected from the group consisting of aluminum, zinc and silicon, and said powdery mixture contains cobalt and said leachable alloy components in the ratio by weight of between 30 and 70 and 75 to 25, (ii) sintering said powdery mixture to form a mechanically stable molding with a density of 1.3 to 5.5 g/cm$^3$, a pore volume of up to 0.5 cm$^3$/g (water adsorption) and a BET surface area (DIN 66 132) of less than 1 m$^2$/g and (iii) activating the sintered molding by at least partial leaching out of said leachable alloy component by means of an alkali hydroxide solution.

2. The process according to claim 1 further comprising converting said cyclohexanone in the presence of an imination catalyst.

3. The process according to claim 2, wherein said imination catalyst is a member selected from the group consisting of acid oxides, zeolites, acid ion exchangers and supported heteropoly acids.

4. The process according to claim 1 wherein said imination reaction is carried out in the presence of a $C_{1-}$ to $C_{-3}$ alcohol.

5. The process according to claim 3, wherein said imination catalyst is used in the form of mechanically stable moldings in a fixed bed reactor.

6. The process according to claim 1 wherein said fixed bed hydrogenation catalyst is arranged in a hydrogenation reactor and the reactor is operated as a trickle bed reactor.

7. The process according to claim 1, wherein said imination reaction is carried out in a fixed bed reactor having a bed of fixed bed imination catalyst arranged above a bed of fixed bed hydrogenation catalyst and the reactor is operated as a trickle bed reactor.

8. The process according to claim 1, wherein said aminating hydrogenation is carried out at a temperature in the range from 90° to 130° C. and a pressure in the range from 5 to 8 MPa.

9. The process according to claim 1, wherein a mixture consisting mainly of 10 to 40 wt. % of said cyclohexanone 10 to 40 wt. % of ammonia and methanol are fed to the imination reaction.

10. The process according to claim 1, further comprising mixing said cyclohexanone, ammonia and alcohol together in a reaction to form an essentially homogeneous solution.

11. The process according to claim 1, further comprising said second step produces a reaction mixture which is treated by distillation to obtain a high-boiling fraction with a higher boiling point than isophorone diamine and containing 3,5,5-trimethyl-6-imino-7-aza-bicyclo-[3,2,1]-octane (=amidine) which is fed to said first stage together with a solution containing isophorone nitrile, ammonia and methanol to enable continuous operation.

* * * * *